(12) United States Patent
Ling et al.

(10) Patent No.: US 8,093,374 B2
(45) Date of Patent: Jan. 10, 2012

(54) BISMUTH HYALURONATE, THE PREPARATION METHOD AND THE USE THEREOF

(75) Inventors: Peixue Ling, Jinan (CN); Yanli He, Jinan (CN); Jianying Chen, Jinan (CN); Jie Liu, Jinan (CN); Tianmin Zhang, Jinan (CN); Xueping Guo, Jinan (CN); Yan Jin, Jinan (CN)

(73) Assignee: Peixue Ling, Shandong (CN)

( * ) Notice: Subject to any disclaimer, the term of this patent is extended or adjusted under 35 U.S.C. 154(b) by 455 days.

(21) Appl. No.: 12/095,797

(22) PCT Filed: Dec. 1, 2006

(86) PCT No.: PCT/CN2006/003241
§ 371 (c)(1),
(2), (4) Date: Jul. 23, 2008

(87) PCT Pub. No.: WO2007/062595
PCT Pub. Date: Jun. 7, 2007

(65) Prior Publication Data
US 2008/0312429 A1    Dec. 18, 2008

(30) Foreign Application Priority Data
Dec. 2, 2005    (CN) .......................... 2005 1 0125667

(51) Int. Cl.
*C08B 37/08*    (2006.01)
(52) U.S. Cl. ...................................................... 536/53

(58) Field of Classification Search ...................... None
See application file for complete search history.

(56) References Cited

U.S. PATENT DOCUMENTS
6,656,921 B1 *   12/2003   Illes et al. ..................... 514/54

FOREIGN PATENT DOCUMENTS
CN    1513882 A *  7/2005
CN    1765937 A *  5/2006

OTHER PUBLICATIONS

Jin, et al., Preparation, Characterization And Anti-Helicobacter Pylori Activity of Bi3+ -Hyaluronate Complex, ScienceDirect, Carbohydrate Polymers 74, 2008, pp. 50-58.

* cited by examiner

*Primary Examiner* — Shaojia Anna Jiang
*Assistant Examiner* — Bahar Schmidtmann
(74) *Attorney, Agent, or Firm* — Dinsmore & Shohl LLP

(57) ABSTRACT

The present invention discloses a bismuth hyaluronate, characterized in that the bismuth content is from 0.5% to 40%, and the glucuronate content is from 20% to 45%, based on dry weight. Also provided is a method for the preparation of said bismuth hyaluronate comprising reaction of a soluble hyaluronate salt with a bismuth salt in a basic aqueous solution, followed by steps of precipitation, filtration, desalting, dehydrating and drying to obtain the product. Further disclosed is the use of the bismuth hyaluronate in the manufacture of a medicament or health foods for preventing and treating gastrointestinal disorders, in particular ulcerous disorders of the GI tract. It has been proven in animal experiments to show a better therapeutic effect than products of the same type.

7 Claims, 1 Drawing Sheet

Figure 1-A. Infrared absorption spectrum (FT-IR) of sodium hyaluronate
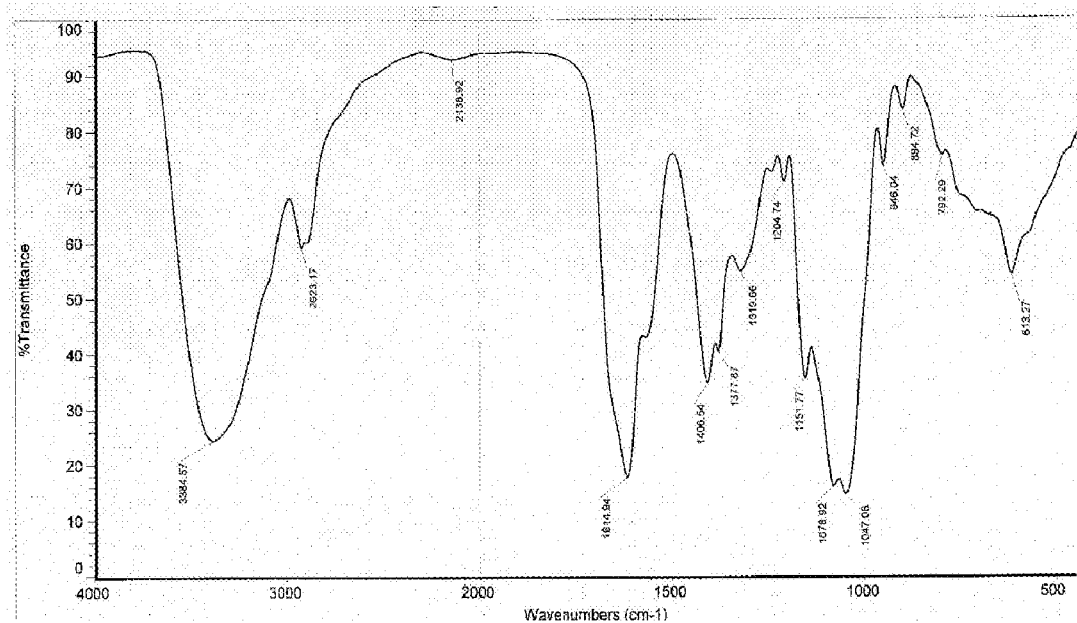
Figure 1-B. Infrared absorption spectrum (FT-IR) of bismuth hyaluronate
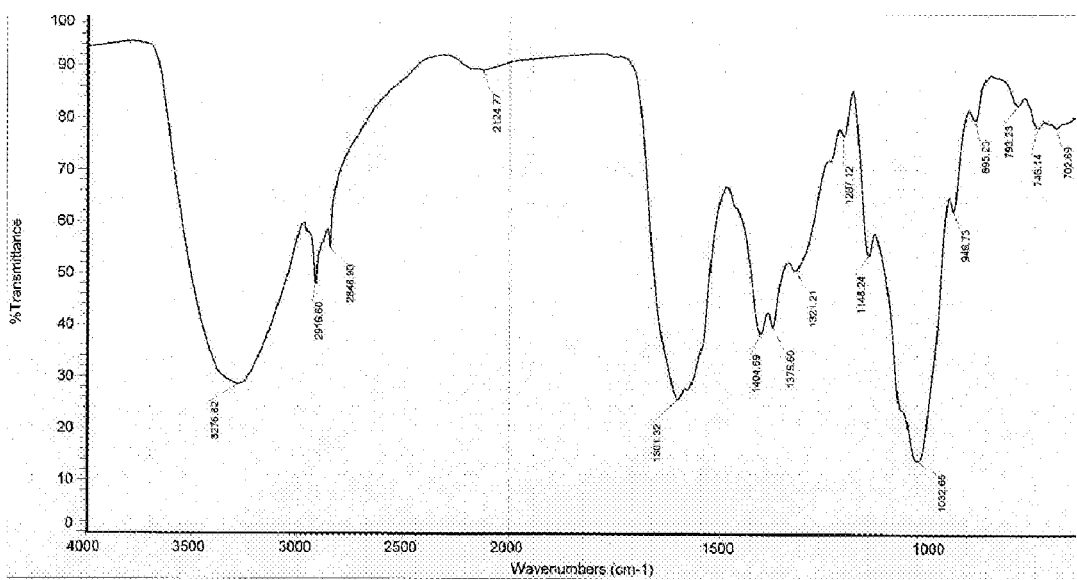

BISMUTH HYALURONATE, THE PREPARATION METHOD AND THE USE THEREOF

TECHNICAL FIELD

The present invention belongs to medical and pharmaceutical fields, and relates to bismuth hyaluronate, the preparation method thereof and the use thereof in the manufacture of a medicament for preventing and treating gastrointestinal disorders and of health foods.

BACKGROUND ART

Hyaluronic acid (HA) is a macromolecular chain polysaccharide consisting of regularly repetitive disaccharide units of D-glucuronate and N-acetylaminoglucose, having a molecular weight ranging from several thousands to several millions. HA has good lubricity, viscoelasticity, and non-immunogenicity and is highly moisturizing. At present, commercially available HA is extracted from animals or prepared from bacterial fermentation, and is used mainly as sodium salt in clinical therapy (such as in opthalmology, orthopedics, dermatology, in prevention of postoperative adhesion, etc.) and in cosmetics. The preparation and use of potassium, calcium, magnesium, aluminum, ammonium, silver and gold salts of hyaluronate have been disclosed in many patents. Hyaluronic acid forms salts (complexes) with ions of Group III metals from the $4^{th}$ period in the periodic table of elements, such as zinc hyaluronate and cobalt hyaluronate, which have been proved to have therapeutic effect on skin ulcers and bedsore (WO9010020). Zinc hyaluronate also possesses significant stomach-protecting activity, and is useful in preventing and treating peptic ulcer (CN1126548). However, bismuth hyaluronate (a complex) and its preparation and use have never been reported in literature.

Gastrointestinal disorders include chronic gastritis, peptic ulcer, functional dyspepsia, gastric cancer and the like, among which peptic ulcer has a high incidence and seriously impairs health of modern people. An epidemiologic investigation in China revealed that 10% of population suffers from this disease during their lifetime, with onset mostly seen in young and middle-aged people (people aging from 20 to 50 accounting for about 70%). The pathogenetic mechanism of peptic ulcer is complicated and not yet fully illuminated. The basic mechanism underlying peptic ulcer may be summarized as imbalance between injury to local GI mucous membrane (ulcerogenic factors) and protection of the mucous membrane (mucosal barrier). When the injury increases or the protection weakens, ulcers occur. Recently, it has been found that the development of peptic ulcer in human is associated with infection by *Helicobacter pylori*.

Currently, the combined use of antibiotics, antacid and mucosa protecting agent is generally accepted as the optimal treatment for peptic ulcer, wherein the mucosa protecting agent is a film-forming, anti-acid substance that is capable of preventing the penetration of gastric acid and pepsin through the mucous membrane, including sucralfate, bismuth compounds, prostaglandin derivatives and the like. The bismuth compounds exhibit high affinities for sulfur, oxygen and nitrogen and strong binding to metallothionein, mucosal glycoproteins, enzyme and peptides. There is evidence indicating its effectiveness in inhibiting the growth of *Helicobacter pylori*. Therefore, bismuth agents are the most frequently used mucosa protecting agent in clinic, among which bismuth potassium citrate, bismuth subsalicylate, bismuth subnitrate, colloidal bismuth pectin and the like are commonly used. The pharmacological effect of bismuth agents may be generalized as follows: forming precipitates in the acid condition within the stomach; adhering to the surface of the gastric mucosa to form a protective layer; protecting the gastric mucosa (in ulcer areas); reducing adverse stimuli to the stomach; promoting the regeneration of ulcerous mucosa and the healing of the ulcer; modulating the secretory action, such as by reducing the activity of pepsin, increasing the secretion of mucoprotein, enhancing release of $PGE_2$ by the mucosa; adsorbing bacteriocins (such as the toxin produced by *Escherichia coli* and the enterotoxin produced by *Vibrio cholerae*); and the direct antibacterial activity against the pathogenic microorganisms (*Helicobacter pylori*).

Biomacromolecular bismuth agents, such as colloidal bismuth pectin, show significantly better therapeutic effect in the treatment of diseases such as gastro-duodenal ulcer, chronic superficial gastritis, chronic atrophic gastritis, alimentary tract hemorrhage and the like than other small molecular ones due to their strong adhesion selectivity, i.e. the specific affinity to the area of gastrointestinal ulcer and the inflaming surface. HA is a biomacromolecular mucopolysaccharide naturally occurring in animal bodies, with no structural differences across species, and has good viscoelasticity, lubricity and film-forming ability. Studies show that HA is involved a number of cellular and physiological processes, such as cell migration and differentiation, wound healing, metastasis of cancer cells, effects on growth factors, embryogenesis and development and inflammation. HA has been experimentally proven to tend to directionally accumulate in sites of inflammation and injury, and macromolecular HA exerts anti-inflammatory activity by inhibiting the function of macrophages. In acid conditions, HA solution shows higher viscosity and formation of macromolecular network structure, and is gel like and strongly adhering. These properties of HA greatly contribute to the use of bismuth hyaluronate as a mucosa protecting agent. Animal experiments shown below demonstrate significantly higher inhibition of acetic acid and acidified ethanol-induced gastric ulcer by bismuth hyaluronate as compared with colloidal bismuth pectin in rats.

CONTENTS OF THE INVENTION

The object of the present invention is to provide a bismuth agent useful in the manufacture of a medicament or health food for the prevention and treatment of gastrointestinal disorders and the preparing method thereof, which bismuth agent is bismuth hyaluronate. Preliminary animal tests proved that bismuth hyaluronate showed a better therapeutic effect in the treatment of gastrointestinal ulcers than colloidal bismuth pectin.

In a first aspect, therefore, the present invention provides a bismuth salt of hyaluronic acid, characterized in that the bismuth content is from 0.5% to 40%, preferably from 15% to 35%, and the glucuronate content is from 20% to 45%, preferably from 20% to 35%, in the dry product.

In a second aspect, the present invention provides a method for the preparation of the bismuth hyaluronate according to the present invention, comprising the steps of:
1) dissolving a bismuth salt in deionized water containing a polyol;
2) dissolving a soluble hyaluronate salt in deionized water, adjusting the resulting solution to an alkaline pH with a solution of potassium hydroxide;
3) slowly adding the solution obtained in step 1) dropwise to the solution obtained in step 2) while maintaining the solution alkaline by adding dropwise a solution of potassium hydroxide, and stirring the reaction;

4) adding ethanol to the solution obtained in step 3) to form precipitate, separating the solid from the liquid; and 5) washing the solid precipitate obtained in step 4) with ethanol, desalting, dehydrating, collecting the precipitate and drying under reduced pressure to give the finished product.

In the above method for the preparation of bismuth hyaluronate, the bismuth salt that may be used includes, but not limited to, bismuth nitrate, bismuth hydroxide, bismuth chloride, bismuth oxide and the like; the polyol that may be used includes, but not limited to, sorbitol, mannitol, glycerol and the like; the soluble hyaluronate salt that may be used includes, but not limited to, the inorganic salts thereof, such as sodium hyaluronate, potassium hyaluronate, calcium hyaluronate, zinc hyaluronate and the like, and the organic salts thereof, such as the quaternary ammonium salt of hyaluronic acid and the like.

In the above method for the preparation of bismuth hyaluronate, acetone or methanol may be used instead of ethanol in step 4) and 5) to carry out the steps of precipitating, desalting and dehydrating.

The bismuth hyaluronate produced according to the present invention is of high purity with low level of impurities. Bismuth hyaluronate is a coordination compound formed by the macromolecule HA and $Bi^{3+}$, in which $Bi^{3+}$ can form from 3 to 10 coordination bonds with elements O and N. A person skilled in the art would recognize that by varying the ratio between the bismuth salt and HA in the reaction, coordination compounds of hyaluronate having different contents of bismuth may be produced. In an embodiment according to the present invention, by modifying the ratio between the reactants, a product with a bismuth content of from 0.5% to 40%, preferably from 15% to 35%, may be obtained. Such variations and modifications of ratios are well within the skill and judgement of those skilled in the art.

The bismuth hyaluronate according to the present invention, having a good biocompatibility and film forming ability, can form a highly viscous collosol in both artificial gastric and intestinal juices. Serving as a protecting layer of the gastrointestinal mucosa, it prevents stimulation of the injured mucosa by foods, gastric acid, digestive enzymes and certain medicaments and facilitates ulcer healing. Due to the tendency of directional accumulation at sites of inflammation and injury and also some anti-inflammatory activity of HA, the bismuth hyaluronate according to the present invention will provide a significantly better therapeutic effect in preventing and treating gastrointestinal disorders as compared with products of the same type. Therefore, the present invention, in a third aspect, provides use of the bismuth hyaluronate according to the present invention in the manufacture of a medicament for preventing and treating gastrointestinal disorders and of health foods.

The bismuth hyaluronate according to the present invention may be orally administered alone or in combination with other functional ingredients, such as other active agents used for the prevention and treatment of gastrointestinal disorders, to prevent and treat gastrointestinal inflammation and gastrointestinal ulcers. It may be associated with conventional adjuvants to formulate into pharmaceutical preparations adapted for oral administration in the form of e.g. tables, pills, capsules, granules, syrups, gels, solutions, suspensions or the like, or health foods, to be used for the prevention and treatment of gastrointestinal disorders, including chronic gastritis, peptic ulcer, functional dyspepsia, gastric cancer and the like, to alleviate symptoms such as pain, diarrhea and dyspepsia, protect the gastrointestinal mucosa, promote regeneration of ulcerous mucosa and ulcer healing, and reduce the development of inflammation, via oral administration.

DESCRIPTION OF THE DRAWINGS

FIG. 1 shows the infrared absorption spectra (FT-IR) of sodium hyaluronate and the bismuth hyaluronate according to the present invention, wherein A represents sodium hyaluronate and B represents the bismuth hyaluronate of the present invention.

SPECIFIC MODE FOR CARRYING OUT THE INVENTION

The present invention will be further described below by way of examples, which, however, are included only for the purpose of illustration and are not to be construed as limiting the scope of present invention.

PREPARATION EXAMPLE 1

100 g of sodium hyaluronate (average molecular weight $1.09 \times 10^6$) was dispersed into 5 L of deionized water, stirred until dissolution. A 10% solution of potassium hydroxide was added dropwise to adjust the pH to between 10 and 12. 133 g of bismuth nitrate [$Bi(NO_3)_3 \cdot 5H_2O$] and 250 g of mannitol were added to 5 L of deionized water, stirred until dissolution, to which the above basic solution of sodium hyaluronate was added slowly with stirring, while maintaining the pH of the reaction at around 12 by adding dropwise a 10% solution of potassium hydroxide. The reaction was further stirred. At end of the reaction, 3 volumes (V/V) of ethanol were added, followed by stirring to effect precipitation. The precipitates were thoroughly washed with an 80% aqueous solution of ethanol. Finally, the precipitates were dehydrated with absolute ethanol, dried under reduced pressure at a temperature of 35° to 40°, to give the finished product, which was determined to have a glucuronate content of 27.9% (W/W) and a bismuth content of 30.7% (W/W), based on dry weight.

PREPARATION EXAMPLE 2

100 g of sodium hyaluronate (average molecular weight $1.41 \times 10^6$) was dispersed into 5 L of deionized water, stirred until dissolution. A 10% solution of potassium hydroxide was added dropwise to adjust the pH to between 10 and 12. 121 g of bismuth nitrate [$Bi(NO_3)_3 \cdot 5H_2O$] and 240 g of sorbitol were added to 5 L of deionized water with stirring until dissolution, to which the above basic solution of sodium hyaluronate was added slowly with stirring, while maintaining the pH of the reaction at around 12 by adding dropwise a 10% solution of potassium hydroxide. The reaction was further stirred. At end of the reaction, 3 to 4 volumes (V/V) of ethanol were added, followed by stirring to effect precipitation. The precipitates were thoroughly washed with an 80% aqueous solution of ethanol. Finally, the precipitates were dehydrated with absolute ethanol, dried under reduced pressure at a temperature of 35° to 40°, to give the finished product, which was determined to have a glucuronate content of 30.1% (W/W) and a bismuth content of 26.3% (W/W), based on dry weight.

PREPARATION EXAMPLE 3

100 g of sodium hyaluronate (average molecular weight $7.5 \times 10^5$) was dispersed into 5 L of deionized water, stirred until dissolution. A 10% solution of potassium hydroxide was added dropwise to adjust the pH to between 10 and 12. 35 g of bismuth hydroxide [Bi(OH)$_3$] was added to 5 L of an aqueous solution containing 60 g of glycerol, to which the above basic solution of sodium hyaluronate was added slowly with stirring, while maintaining the pH of the reaction at around 12 by adding dropwise a 10% solution of potassium hydroxide. The reaction was further stirred. At end of the reaction, 2 to 3 volumes (V/V) of acetone were added, and precipitation occurred. The precipitates were thoroughly washed with a 70% to 80% aqueous solution of acetone. Finally, the precipitates were dehydrated with acetone, dried under reduced pressure at a temperature of 35° to 40°, to give the finished product, which was determined to have a glucuronate content of 34.7% (W/W) and a bismuth content of 16.9% (W/W), based on dry weight.

As described above, bismuth hyaluronate is a coordination compound formed by biomacromolecule HA and Bi$^{3+}$. Bi$^{3+}$ may form 3 to 10 coordination bonds with element O, N of HA, which itself is a mixture. Under current conditions, it is not yet possible to confirm the exact structure of bismuth hyaluronate. By way of example, the structure of colloidal bismuth subcitrate (CBS), which has long been used clinically, has not yet been ascertained (Abrams M J and Murrer. B A., Metal compounds in therapy and diagnosis. Science, 1993; 261: 725-730; I. Bertini, H. B. Gray & J. S. Valentine, Eds. METALS IN MEDICINE. In press: Biological Inorganic Chemistry: Structure & Reactivity, University Science Books, Mill Valley, Calif., Publ.; Pharmacopeia of People's Republic of China, 2005, 2$^{nd}$ edition). The present inventors performed FT-IR on the starting material (i.e. sodium hyaluronate) and the product (i.e. the bismuth hyaluronate of present invention) (equipment: Nicolet NEXUS 470 FT-IR Spectrometer). The results are shown in FIG. 1. The formation of coordination bonds within bismuth hyaluronate was confirmed by variation in absorption peaks (see FIG. 1 and Table 1 below). The glucuronate content given in the above Examples is representative of the amount of hyaluronic acid, and the bismuth content given represents the amount of element bismuth that coordinates with elements O and N of HA molecules.

TABLE 1

Data of FT-IR analysis of sodium hyaluronate and bismuth hyaluronate

| Mode of Vibration | Position of Absorption Peak of HA/cm$^{-1}$ | Position of Absorption Peaks of Bismuth Hyaluronate/cm$^{-1}$ |
| --- | --- | --- |
| $V_{OH}$ | 3384.57 | 3276.62 |
| $V_{C=O}$ | 1614.94 | 1601.32 |
| $V_{C-N}$ | 1047.06 | 1032.65 |

EXPERIMENTAL EXAMPLES

The results from preliminary pharmacodynamic tests of the bismuth hyaluronate according to the present invention are as follows.

1. Protecting Effect of bismuth hyaluronate on acetic acid-induced Gastric Ulcer in Rats Female Wistar rats weighing 150 to 200 g were used. Following the method described in literatures ((1) Pharmacological Test Methodology, 2$^{nd}$ edition, Beijing, People's Health Press, 1991, 1158-1160; (2) Guidelines for preclinical studies of new drugs (western medicines) (pharmacy, pharmacology, toxicology), 1993, 88-89), a model of acetic acid-induced gastric ulcer was made. Specifically, in an area of 5 mm in diameter on the serosal side of the body of stomach in rats under anesthesia with ether, gastric ulcer was induced by treatment with 0.2 ml of glacial acetic acid for 1.5 min. On the next day following the operation, animals were randomly divided into 6 groups and started on oral administration, with distilled water as negative control and colloidal bismuth pectin as positive control. The test samples are the bismuth hyaluronate of the present invention prepared according to the Preparation Example 1 (having a glucuronate content of 27.9% and a bismuth content of 30.7%) and the starting material sodium hyaluronate (having an average molecular weight of 9.1×10$^5$ and a glucuronate content of 38.9%). The rats received intragastric administration once daily in a volume of about 10 ml for 10 consecutive days. Then the animals were sacrificed, and their stomachs were removed and fixed in a formaldehyde solution. After dissection, the size of the gastric ulcer was determined by measuring under microscope the maximum longitudinal diameter ($d_1$) and the maximum transverse diameter ($d_2$) through the center of the ulcer, and calculating the area of ulcer using the following equation: $S=\pi \times (d_1/2) \times (d_2/2)$. The inhibition of ulcer was expressed as the percentage of the control. The results are listed in the Table below.

Table 2. Protecting Effect of bismuth hyaluronate on acetic-induced Gastric Ulcer in Rats

TABLE 2

Protecting effect of bismuth hyaluronate on aacetic acid-induced gastric ulcer in rats

| Group | Number of Animals | Dose (mg/kg) | Area of Ulcer ($\bar{x} \pm s$) (mm$^2$) | Inhibition of Ulcer (%) |
| --- | --- | --- | --- | --- |
| Negative Control (Distilled water) | 10 | — | 15.71 ± 2.20 | — |
| Positive Control (colloidal bismuth pectin) | 9 | 150 | 7.15 ± 2.03* | 54.48 |
| Bismuth Hyaluronate (high dose) | 8 | 150 | 4.05 ± 1.62***$^{\Delta\Delta}$ | 74.22 |
| Bismuth Hyaluronate (medium dose) | 9 | 100 | 4.98 ± 1.15***$^{\Delta}$ | 68.30 |
| Bismuth Hyaluronate (low dose) | 7 | 50 | 5.92 ± 2.27** | 62.32 |
| Sodium Hyaluronate | 9 | 150 | 10.25 ± 2.29 | 34.75 |

*$P < 0.05$ vs. negative control.
**$P < 0.01$ vs. negative control
***$P < 0.001$ vs. negative control
$^{\Delta}P < 0.05$ vs. positive control
$^{\Delta\Delta}P < 0.01$ vs. positive control 2. Prevention and Treatment of hydrochloric acid-ethanol-induced Injury to Gastric Mucosa by bismuth hyaluronate Female Wistar rats weighing 150 to 200 g were used. Following the method described in the literature (Methodology of pharmacological studies of Chinese medicines, Beijing, People's Health Press, 1994: 441). The rats were fasted, with access to water, for 24 h. Then the rats were randomly divided (see above) and received intragastric administration. 30 min after the administration, each rat was drenched with hydrochloric acid-ethanol (a mixture of 50 ml of absolute ethanol and 1 ml of concentrated hydrochloric acid) at a dose of 0.5 ml/100 g of body weight. 1 h after the treatment with acidified ethanol, the animals were sacrificed, and their stomachs were removed and fixed in a formaldehyde solution. The stomach was cut open along the greater curvature and washed for examination of the injury to the gastric mucous membrane. The lengths of strip-like hemorrhagic injuries were measured and the results are reported in the table below.

TABLE 3

Prevention and treatment of hydrochloric acid-ethanol-induced injury to gastric mucosa by bismuth hyaluronate in rats

| Group | Number of Animals | Dose (mg/kg) | Length of injury ($\bar{x} \pm s$) (mm) | Inhibition of Ulcer (%) |
|---|---|---|---|---|
| Negative Control (Distilled water) | 9 | — | 97.50 ± 13.28 | — |
| Positive Control (colloidal bismuth pectin) | 7 | 150 | 43.64 ± 9.55** | 55.24 |
| Bismuth Hyaluronate (high dose) | 12 | 150 | 7.11 ± 2.13***△△△ | 92.70 |
| Bismuth Hyaluronate (medium dose) | 10 | 100 | 6.89 ± 1.86***△△△ | 92.93 |
| Bismuth Hyaluronate (low dose) | 9 | 50 | 26.54 ± 7.88***△△ | 72.78 |
| Sodium Hyaluronate | 8 | 150 | 50.54 ± 11.98* | 48.16 |

*$P < 0.05$ vs. negative control.
**$P < 0.01$ vs. negative control
***$P < 0.001$ vs. negative control
△$P < 0.05$ vs. positive control
△△$P < 0.01$ vs. positive control
△△△$P < 0.001$ vs. positive control The above results indicate that the bismuth hyaluronate according to the present invention exhibited a statistically significant inhibition of acetic acid- and acidified ethanol-induced gastric ulcer in rats, and the inhibition was significantly higher than the positive control colloidal bismuth pectin.

The invention claimed is:
1. A composition comprising bismuth hyaluronate complex wherein the bismuth content is from 15% to 35%, and the glucuronate content is from 20% to 35%, based on dry weight.
2. A method for the preparation of bismuth hyaluronate complex comprising the steps of:
   dissolving a bismuth salt in deionized water containing a polyol to form a first solution;
   dissolving a soluble hyaluronate salt in deionized water and adjusting the resulting solution to an alkaline pH with a solution of potassium hydroxide to form a second solution;
   adding said first solution to said second solution while maintaining said second solution alkaline by adding potassium hydroxide, and stirring the reaction;
   adding a precipitating agent to said second solution to form precipitates;
   separating said precipitates from the liquid; and
   washing said precipitates with said precipitating agent, desalting, dehydrating, collecting said precipitates and drying said precipitates under reduced pressure to yield a bismuth hyaluronate composition wherein the bismuth content is from 15% to 35%, and the glucuronate content is from 20% to 35%, based on dry weight.
3. A method as claimed in claim 2 wherein said bismuth salt is bismuth nitrate, bismuth hydroxide, bismuth chloride, or bismuth oxide.
4. A method as claimed in claim 2 wherein said polyol is sorbitol, mannitol, or glycerol.
5. A method as claimed in claim 2 wherein said soluble hyaluronate salt is an inorganic salt or an organic salt.
6. A method as claimed in claim 5 wherein the inorganic hyaluronate salt is sodium hyaluronate, potassium hyaluronate, calcium hyaluronate or zinc hyaluronate, and the organic hyaluronate salt is quaternary ammonium hyaluronate.
7. A method as claimed in claim 2, wherein said precipitating agent comprises acetone, methanol or ethanol.

* * * * *